(12) United States Patent
He et al.

(10) Patent No.: US 11,007,060 B2
(45) Date of Patent: May 18, 2021

(54) TRANSAPICALLY-IMPLANTED MITRAL VALVE FLEXIBLE COAPTATION PLATE BLOCKING BODY AND IMPLANTATION METHOD

(71) Applicant: Shanghai Joy Medical Devices Co., Ltd., Shanghai (CN)

(72) Inventors: Zhaoming He, Zhenjiang (CN); Teng Jing, Zhenjiang (CN); Kailiang Zhang, Zhenjiang (CN)

(73) Assignee: SHANGHAI JOY MEDICAL DEVICES CO., LTD., Shanghai (CN)

( * ) Notice: Subject to any disclaimer, the term of this patent is extended or adjusted under 35 U.S.C. 154(b) by 81 days.

(21) Appl. No.: 16/086,508

(22) PCT Filed: Dec. 7, 2016

(86) PCT No.: PCT/CN2016/108785
§ 371 (c)(1),
(2) Date: Sep. 19, 2018

(87) PCT Pub. No.: WO2017/177701
PCT Pub. Date: Oct. 19, 2017

(65) Prior Publication Data
US 2019/0117386 A1    Apr. 25, 2019

(30) Foreign Application Priority Data
Apr. 14, 2016   (CN) .......................... 201610229742.0

(51) Int. Cl.
*A61F 2/24*     (2006.01)
*A61B 17/00*    (2006.01)

(52) U.S. Cl.
CPC .............. *A61F 2/246* (2013.01); *A61B 17/00* (2013.01); *A61F 2/24* (2013.01); *A61F 2/2418* (2013.01);
(Continued)

(58) Field of Classification Search
CPC ...... A61F 2/2487; A61F 2/2445; A61F 2/246; A61F 2230/0026; A61F 2220/0083;
(Continued)

(56) References Cited

U.S. PATENT DOCUMENTS

| 4,692,164 A | 9/1987 | Dzemeshkevich et al. |
| 2003/0199975 A1 | 10/2003 | Gabbay |

(Continued)

FOREIGN PATENT DOCUMENTS

| CN | 1131384 A | 9/1996 | |
| CN | 104055605 A | * 9/2014 | ........... A61F 2/2445 |

(Continued)

OTHER PUBLICATIONS

Translation of CN 104055605 (Year: 2014).*

(Continued)

*Primary Examiner* — Brian E Pellegrino
(74) *Attorney, Agent, or Firm* — Fox Rothschild LLP; Carol E. Thorstad-Forsyth (57) ABSTRACT

A transapically-implanted mitral valve flexible closure plate blocking body comprising: a flexible closure plate (7), a left and right guide wire (8), a guide ring (13) and a fixation plug (12). The fixation plug (12) is fixedly implanted at a cardiac apex (4) of the heart, the flexible closure plate (7) is located at an anterior and posterior leaflet junction of the heart, the left and right guide wire (8) respectively pass through a hook (6) on the same side, are fixedly connected to the flexible closure plate (7) in the upper portion on the same side, and respectively pass through a guide ring (13) fixedly connected in the lower portion of the flexible closure plate (7) on the same side, and are fixedly connected to the fixation plug (12). An implantation method thereof is also provided.

9 Claims, 5 Drawing Sheets

(52) U.S. Cl.
CPC .... *A61F 2/2445* (2013.01); *A61F 2210/0014* (2013.01); *A61F 2220/0025* (2013.01)

(58) Field of Classification Search
CPC ........... A61F 2220/0025; A61F 2/2439; A61B 17/00; A61B 17/12122; A61B 17/0057; A61B 17/0487; A61B 2017/00349; A61B 17/32056
See application file for complete search history.

(56) References Cited

U.S. PATENT DOCUMENTS

| | | |
|---|---|---|
| 2005/0038509 A1 | 2/2005 | Ashe |
| 2010/0262233 A1 | 10/2010 | He |
| 2012/0101571 A1* | 4/2012 | Thambar ............ A61B 17/0057 623/2.17 |
| 2012/0197388 A1 | 8/2012 | Khairkhahan et al. |
| 2012/0253457 A1 | 10/2012 | Winston et al. |
| 2013/0023985 A1 | 1/2013 | Khairkhahan et al. |
| 2014/0067048 A1 | 3/2014 | Chau et al. |
| 2015/0094800 A1 | 4/2015 | Chawla |
| 2016/0089238 A1 | 3/2016 | Centola et al. |
| 2017/0065418 A1* | 3/2017 | Skarsgard ............. A61F 2/2487 |
| 2017/0112618 A1 | 4/2017 | Li et al. |
| 2017/0151057 A1 | 6/2017 | He et al. |

FOREIGN PATENT DOCUMENTS

| | | |
|---|---|---|
| CN | 105852916 A | 8/2016 |
| SU | 1205905 A1 | 1/1986 |
| WO | 2010/125591 A1 | 11/2010 |

OTHER PUBLICATIONS

First Office Action received for Chinese Patent Application No. 201610229742.0 and translation.
Extended European Search Report issued in EP 16898513.3 dated Nov. 14, 2019.

* cited by examiner

TRANSAPICALLY-IMPLANTED MITRAL VALVE FLEXIBLE COAPTATION PLATE BLOCKING BODY AND IMPLANTATION METHOD

CROSS REFERENCE TO RELATED APPLICATION

The present application is the U.S. national stage of PCT International Patent Application No. PCT/CN2016/108785 filed on Dec. 7, 2016, which claims priority to Chinese Patent Application No. 201610229742.0 filed on Apr. 14, 2016. All of the aforementioned applications are incorporated herein by reference in their entireties.

TECHNICAL FIELD

The present invention relates to the field of human heart repair technology and medical instruments, in particular to an instrument capable of repairing mitral valve regurgitation of the heart.

BACKGROUND ART

Figure 1:
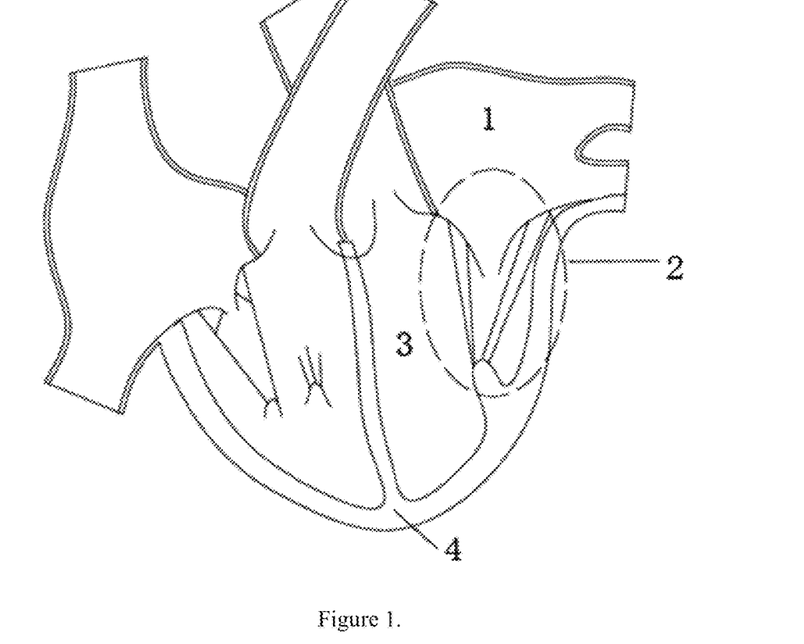
FIG. 1 is a view of the structure of the heart and the position of the mitral valve.

The human heart and valve are shown in FIG. 1. The left ventricle 3 is located at the upper left of the cardiac apex 4, the mitral valve 2 is located between the left atrium 1 and the left ventricle 3, and the mitral valve 2 controls the unidirectional flow of blood from the left atrium 1 into the left ventricle 3. The dysfunctional mitral valve 2 may cause the two leaflets of the mitral valve 2 to be incompletely closed, causing the blood to flow back from the left ventricle 3 to the left atrium during systoles. Mitral valve regurgitation will cause pulmonary congestion and left ventricular 3 hypertrophy, which ultimately leads to heart failure and death of patients.

Figure 2:
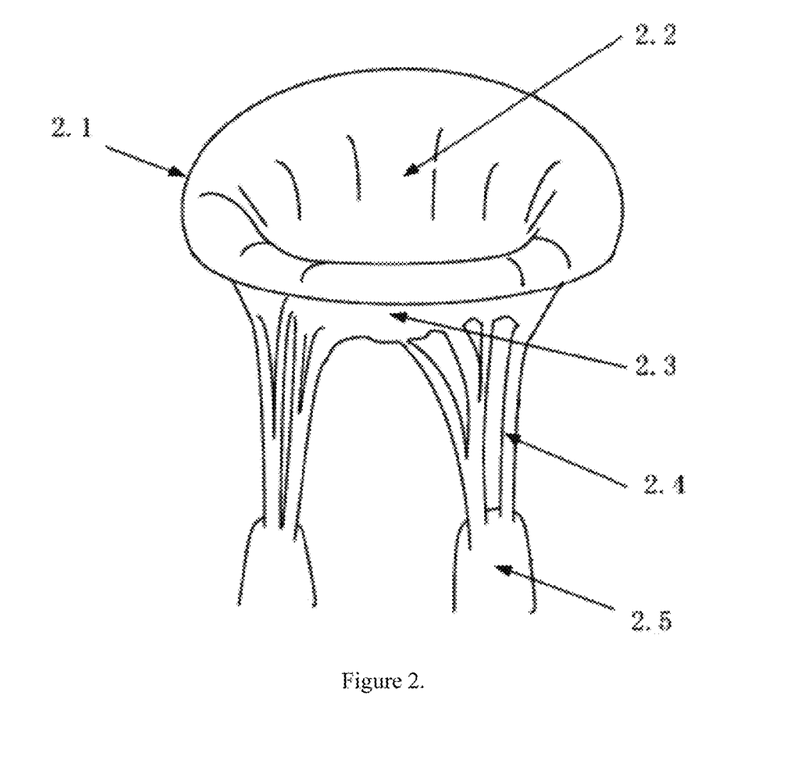
FIG. 2 is an enlarged view of the tissue structure of the mitral valve in FIG. 1.

The structure of the mitral valve 2 is shown in FIG. 2. The mitral valve 2 is a complex one-way valve structure that withstands blood pressure, consisting of a mitral valve annulus 2.1, an anterior leaflet 2.2, a posterior leaflet 2.3, chordae 2.4, papillary muscles 2.5 and myocardium on the left ventricular wall. The papillary muscles 2.5 are attached to the left ventricular wall. The anterior leaflet 2.2 and the posterior leaflet 2.3 are attached to the mitral valve annulus 2.1. The mitral valve annulus 2.1 is an internal tissue structure that connects the anterior leaflet 2.2, the posterior leaflet 2.3, and the left ventricular wall. According to the tissue structure of the mitral valve annulus 2.1, it is divided into a fibrous layer of the anteromedial segment and a muscle layer of the posterior-lateral segment. The chordae 2.4 start from the papillary muscles 2.5 and are attached to the leaflets to prevent the anterior leaflet 2.2 and the posterior leaflet 2.3 from prolapsing into the left atrium when the heart contracts.

Figure 3:
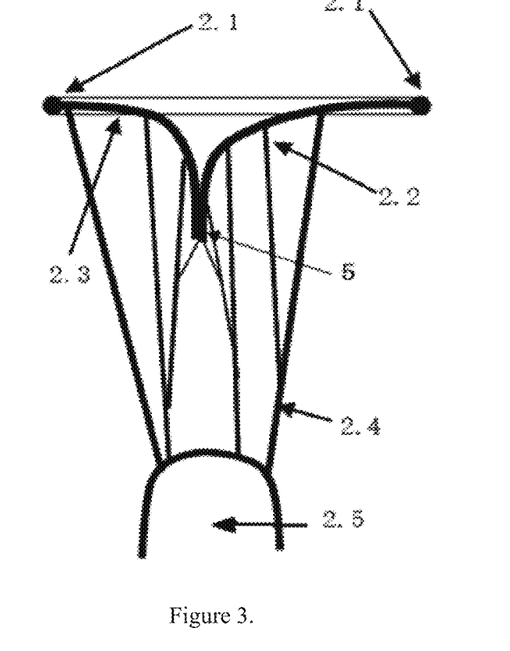
FIG. 3 is a right side view of the mitral valve in FIG. 2 when the mitral valve is closed.
Figure 4:
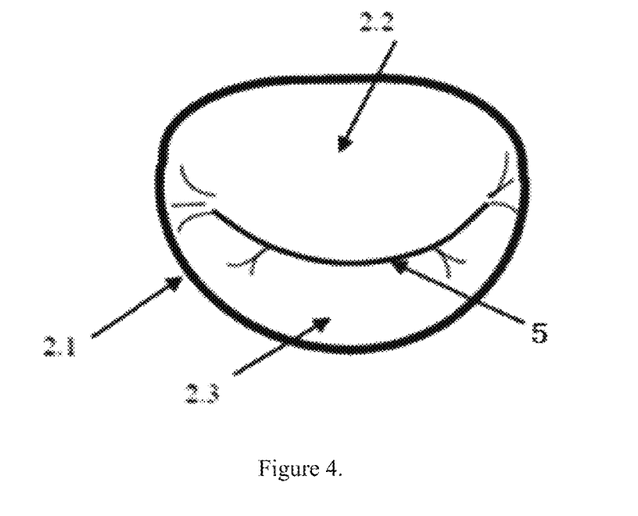
FIG. 4 is a partial enlarged view of the atrium in FIG. 2 when the mitral valve is closed.
Figure 5:
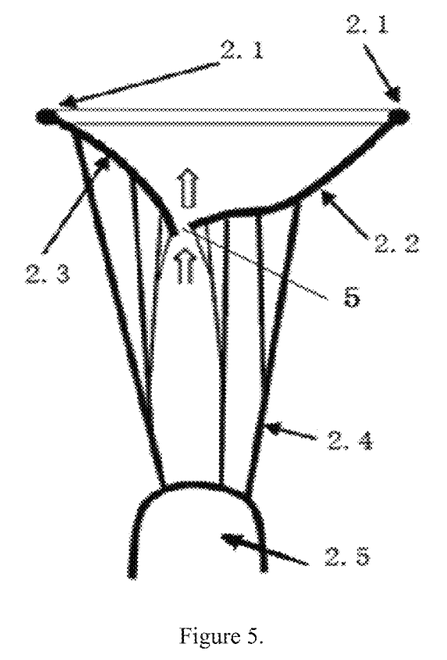
FIG. 5 is a right side view of the mitral valve regurgitation in incomplete closure of the mitral valve during systoles in FIG. 2.
Figure 6:
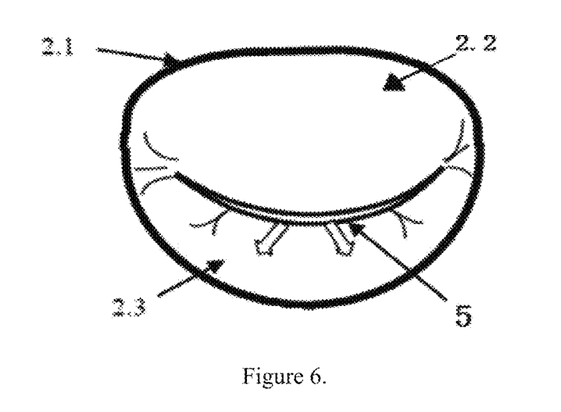
FIG. 6 is a partial enlarged view of the atrium in mitral valve regurgitation in incomplete closure of the mitral valve during systoles in FIG. 2.

The state of a normal mitral valve during closure is as shown in FIG. 3 and FIG. 4. After the mitral valve is closed, there is no gap between the anterior leaflet 2.2 and the posterior leaflet 2.3, and the anterior and posterior leaflet junction 5 is completely closed with no regurgitation. When the state of the mitral valve 2 during closure is as shown in FIG. 5 and FIG. 6, a gap exists between the anterior and posterior leaflet junction 5 of the mitral valve 2. The gap between the anterior and posterior leaflet junction 5 causes the blood to flow from the left ventricle 3 back to the left atrium 1 (as indicated by the arrow in FIG. 5) when the heart contracts. Such flow-back is called mitral valve regurgitation, which reduces heart efficiency and causes heart failure.

At present, for the treatment of mitral valve regurgitation, there are mainly annuloplasty, mechanical mitral valve or bioprosthetic mitral valve transplantation, etc., most of which need to open the chest, open the heart, which causes big trauma to the human body, and has low reliability, resulting in 50% of mitral valve regurgitation recurrence within 5 years after treatment. The existing advanced minimally invasive treatment method is to clamp the midpoints of the anterior and posterior leaflet edges together through a mitral valve clamp (MitraClip, Abbott, USA) to form two independent blood flow channels to reduce blood regurgitation, but this method has residual regurgitation.

SUMMARY OF THE INVENTION

An objective of the present invention is to solve the problems existing in the prior art mitral valve regurgitation treatment method. The present invention provides a transapically-implanted mitral valve flexible closure plate blocking body for repairing mitral valve regurgitation, blocking the regurgitation gap of the mitral valve and effectively preventing regurgitation of the mitral valve. The present invention also provides a method for implanting the mitral valve flexible closure plate blocking body, which is implanted into the regurgitation gap position of the mitral valve at the anterior and posterior leaflet joint by minimally invasive surgery. It does not need to open the chest or the heart, has little trauma to the human body, has no residual regurgitation, and has high reliability.

In order to achieve the above objective, the technical solution adopted by the transapically-implanted mitral valve flexible closure plate blocking body according to the present invention is: the mitral valve flexible closure plate blocking body comprises a flexible closure plate, a left and right guide wire, a left and right guide ring and a fixation plug, wherein the fixation plug is fixedly implanted at a cardiac apex of the heart, the flexible closure plate is located at an anterior and posterior leaflet commissures of the heart, each of the left and right mitral valve annulus at the anterior and posterior leaflet commissures is fixedly implanted with a hook, the left and right guide wire respectively pass through the hook on the same side and are fixedly connected to the flexible closure plate in the upper portion on the same side, a lower left portion and a lower right portion of the flexible closure plate are fixedly connected with one guide ring each, and the left and right guide wire respectively pass through the guide ring on the same side and are fixedly connected to the fixation plug.

Further, the flexible closure plate has a longitudinal cross section of an inverted isosceles trapezoidal structure and the flexible closure plate can be rolled into an elongated cylinder along the upper base or the lower base.

Further, a support rod is embedded in the edge of the lower base of the flexible closure plate along the lengthwise direction of the lower base, the lower base of the flexible closure plate is fixedly connected to one end of a pull wire, and the other end of the pull wire is fixedly connected to the fixation plug.

Further, there is a plurality of pull wires, the plurality of pull wires have one end uniformly connected to the flexible closure plate along the lengthwise direction of the lower base of the flexible closure plate, and the other end of the plurality of pull wires is fixedly connected to the fixation plug.

The technical solution adopted by the method for implanting a transapically-implanted mitral valve flexible closure plate blocking body is: a small incision is made at the cardiac apex position on the left of the chest to the cardiac apex position to perform a purse-string operation, a cardiac apex cannula is inserted into the left ventricle from the purse string, and the purse string is tightened to fix the cardiac apex cannula, further comprising the following steps:

A. each of the left and right guide wire threads the hook, the hook is placed in a hook implantation catheter, the hook implantation catheter enters the left ventricle through the cardiac apex cannula and reaches the anterior and posterior leaflet commissures, the hook is pushed out from the hook implantation catheter by a push rod, so that the hook is inserted into the mitral valve annulus; two hooks are respectively implanted in the left and right mitral valve annulus at the anterior and posterior leaflet commissure; and the hook implantation catheter is withdrawn after the two hooks are implanted, and two ends of each of the left and right guide wire passing through the hook are led through a cardiac apex catheter;

B. in vitro, the flexible closure plate and the guide ring are integrally formed into one whole piece, one end of each of the left and right guide wires is fixedly connected with the upper portion of the flexible closure plate on the same side, respectively, and the other end passes through the guide ring on the same side; the flexible closure plate is then crimped into a cylinder, the entire piece of the cylinder is placed in a closure plate implantation catheter, the closure plate implantation catheter enters into the left ventricle through the cardiac apex cannula, the flexible closure plate is pushed out to deploy, the left and right guide wires passing through the guide ring are led through the closure plate implantation catheter, and finally the left and right guide wires are tensioned so that the upper left and upper right portions of the flexible closure plate are respectively located at the hook position on the same side; and C. the closure plate implantation catheter is withdrawn, the cardiac apex cannula is removed, and the left and right guide wires are tightened with the fixation plug.

Further, in step B, the lower base of the flexible closure plate is fixedly connected to one end of the pull wire, while the support rod is fixedly embedded in the edge of the lower base of the flexible closure plate, and the flexible closure plate together with the guide ring, the support rod and one end of the pull wire is placed in the closure plate implantation catheter.

With the above technical solution adopted by the present invention, there are the following advantages: the flexible closure plate in the mitral valve flexible closure plate blocking body of the present invention is made from a flexible material with excellent ductility, is implanted via a small incision on the left side of the chest, enters the left ventricle via the cardiac apex, and is placed and fixed at a regurgitation hole position of the anterior and posterior leaflet commissures of the mitral valve. During diastoles, the mitral valve opens, and blood flows from the left atrium to the left ventricle via two channels between the anterior and posterior leaflets and the closure plate. During systoles, the anterior and posterior leaflets close, the edges of the leaflets squeeze the closure plate so that the plate deforms slightly, and the edges of the leaflets and the slightly deformed closure plate are tightly bound together, thereby blocking a regurgitation channel of the mitral valve, and effectively preventing regurgitation of the mitral valve. The flexible closure plate blocking body is simple in structure and highly reliable, the implantation method thereof causes little trauma of the body, and the residual regurgitation rate is low. The present invention treats diseases such as functional mitral valve insufficiency, and the success rate for repairing functional mitral valve regurgitation is more than 90%.

BRIEF DESCRIPTION OF THE DRAWINGS

The present invention will be further described below in conjunction with the drawings and specific embodiments, but the scope of the present invention is not limited thereto.

In the drawings: 1—left atrium, 2—mitral valve, 2.1—mitral valve annulus, 2.2—anterior leaflet, 2.3—posterior leaflet, 2.4—chordae, 2.5—papillary muscle, 3—left ventricle, 4—cardiac apex, 5—anterior and posterior leaflet junction, 6—hook, 6.1—barb, 6.2—connecting ring, 7—flexible closure plate, 8—guide wire, 9—hook implantation catheter, 10—pull wire, 11—closure plate implantation catheter, 12—fixation plug, 13—guide ring, 14—support rod.

DETAILED DESCRIPTION OF THE PRESENT INVENTION

Figure 7:
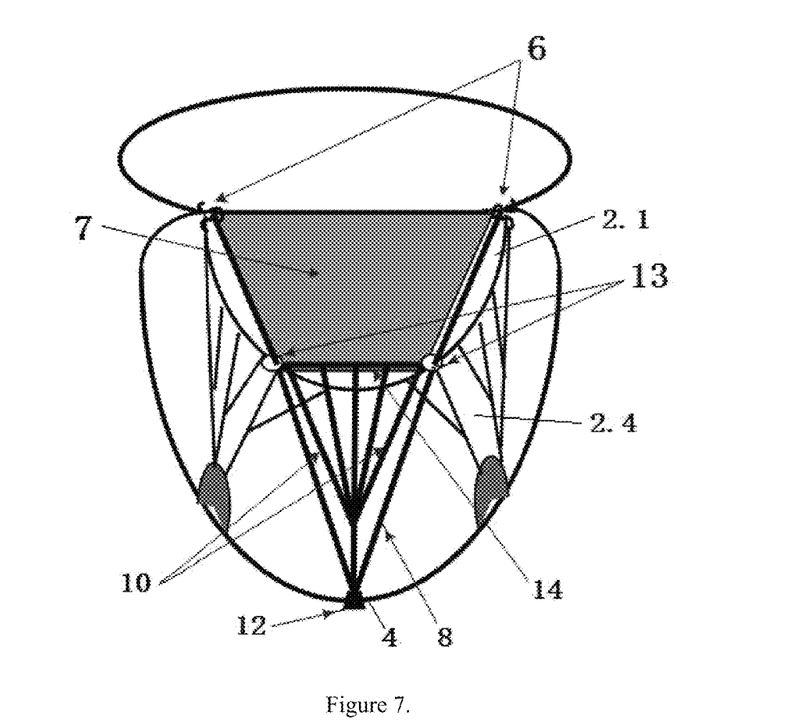
FIG. 7 is a schematic view of a transapically-implanted mitral valve flexible closure plate blocking body after implantation according to the present invention.

Referring to FIG. 7, the structure of a transapically-implanted mitral valve flexible closure plate blocking body comprises a hook 6, a flexible closure plate 7, a guide wire 8, a pull wire 10, a guide ring 13, a support rod 14 and a fixation plug 12. The fixation plug 12 is implanted at a cardiac apex 4. There are two hooks 6, which are implanted in the left and right positions on a mitral valve annulus 2.1 at an anterior-posterior leaflet junction 5, respectively. The flexible closure plate 7 is made from a flexible material with excellent ductility. The longitudinal section thereof has an inverted isosceles trapezoidal structure with a front and rear thickness of 5-6 mm. The length of the upper base of the isosceles trapezoid is longer than that of the lower base. The flexible closure plate 7 is capable of being tightly crimped into an elongated cylinder along their mutually parallel upper or lower base edges. The flexible closure plate 7 is placed between the anterior and posterior leaflets of the mitral valve of the heart after implantation. At the anterior and posterior leaflet junction of the free edges of an anterior leaflet 2.2 and a posterior leaflet 2.3, the flexible closure plate 7 is used to block a regurgitation channel formed by the incomplete closure of the two leaflets. One guide ring 13 is fixedly connected to each of the lower left portion and the lower right portion of the flexible closure plate 7. There are two guide wires 8 on the left and the right. The two guide wires 8 on the left and the right respectively pass through the hook 6 on the same side. The guide wire 8 is fixedly connected to the upper portion of the flexible closure plate 7 on the same side. That is, the upper left portion of the flexible closure plate 7 is fixedly connected to the hook 6 on the left side via a first guide wire 8, and the upper right portion of the flexible closure plate 7 is fixedly connected to the hook 6 on the right side via a second guide wire 8. The left and right guide wires 8 simultaneously pass through the guide ring 13 on the same side and then extend downwardly to the fixation plug 12 at the cardiac apex 4 or a papillary muscle 2.5. That is, the first guide wire 8 passes through the guide ring 13 on the left side and then extends downwardly to be fixedly connected to the fixation plug 12, and the second guide wire 8 passes through the guide ring 13 on the right side and then extends downwardly to be fixedly connected to the fixation plug 12. The guide ring 13 serves to define the orientation of the guide wire 8.

The lower base of the flexible closure plate 7 is fixedly connected to one end of the pull wire 10, and the other end of the pull wire 10 is fixedly connected to the fixation plug 12. In the present invention, there is a plurality of pull wires 10. One end of the plurality of pull wires 10 is uniformly connected to the flexible closure plate 7 along the lengthwise direction of the lower base of the flexible closure plate 7, and the other end of the plurality of pull wires 10 is fixedly connected to the fixation plug 12. The position of the flexible closure plate 7 is fixed by the pull wire 10. Thus, the flexible closure plate 7 is placed in the optimal position via the hook 6, the pull wire 10 and the fixation plug 12.

One support rod 14 is embedded in the edge of the lower base of the flexible closure plate 7 along the lengthwise direction of the lower base to maintain the support rod 14 parallel to the lower base of the flexible closure plate 7. The support rod 14 is used to support the flexible closure plate 7 to prevent the flexible closure plate 7 from being bent and deformed when the pull wire 10 pulls the flexible closure plate 7.

The hook 6 is made from a nickel-titanium memory alloy material. The guide wire 8 and the pull wire 10 are made from an ePTFE (expanded polytetrafluoroethylene) material. The support rod 14 is made from a rigid material. The flexible closure plate 7 is made from a flexible, blood-compatible flexible material with excellent ductility. The fixation plug 12 is made from a blood-compatible material. The fixation plug 12 can lock the guide wire 8 and the pull wire 10 and fix them at the position of the cardiac apex 4 or the papillary muscles 2.5. The blood-compatible material is a polyurethane or pericardial material. The flexible closure plate 7 can be made from polyurethane.

Figure 8:
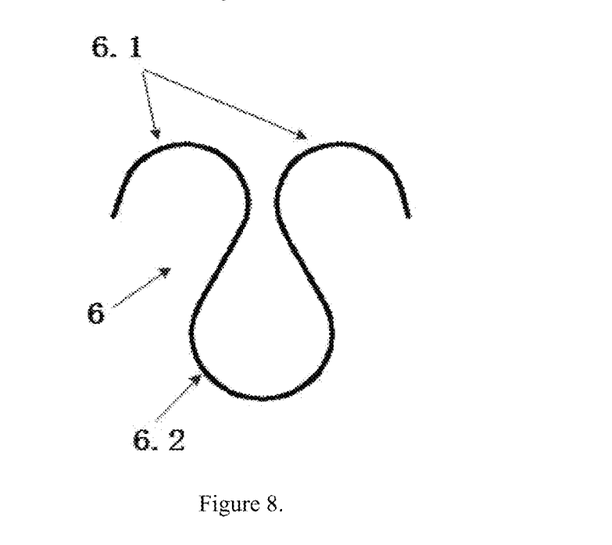
FIG. 8 is an enlarged view of the structure of a hook in FIG. 7.

Referring to FIG. 8, the hook 6 is composed of two portions, a barb 6.1 and a connecting ring 6.2. At one end are two barbs 6.1, and at the other end is one connecting ring 6.2. When the hook 6 is implanted, the barb 6.1 portion is fixed to the mitral valve annulus 2.1. The guide wire 8 threads the connecting ring 6.2 and is fixedly connected to the flexible closure plate 7. The flexible closure plate 7 is secured to the hook 6 by the guide wire 8.

Figure 9:
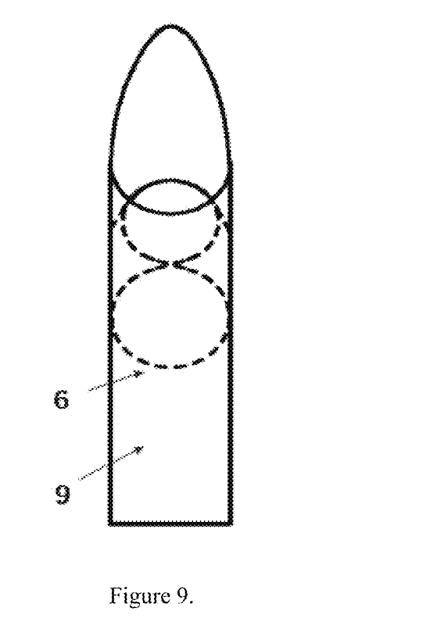
FIG. 9 is a schematic view of the hook placed in a hook implantation catheter in FIG. 8.

Referring to FIG. 9, before the hook 6 is implanted into the heart, the hook 6 is first placed into a hook implantation catheter 9. The inner diameter of the hook implantation catheter 9 is adapted to the outer diameter of the connecting ring 6.2 of the hook 6. When the hook 6 is placed, the barb 6.1 portion is slightly bent and placed in the front end of the hook implantation catheter 9.

Referring to FIGS. 1-10, the method for implanting the mitral valve flexible closure plate blocking body into the heart is as follows.

Figure 10:
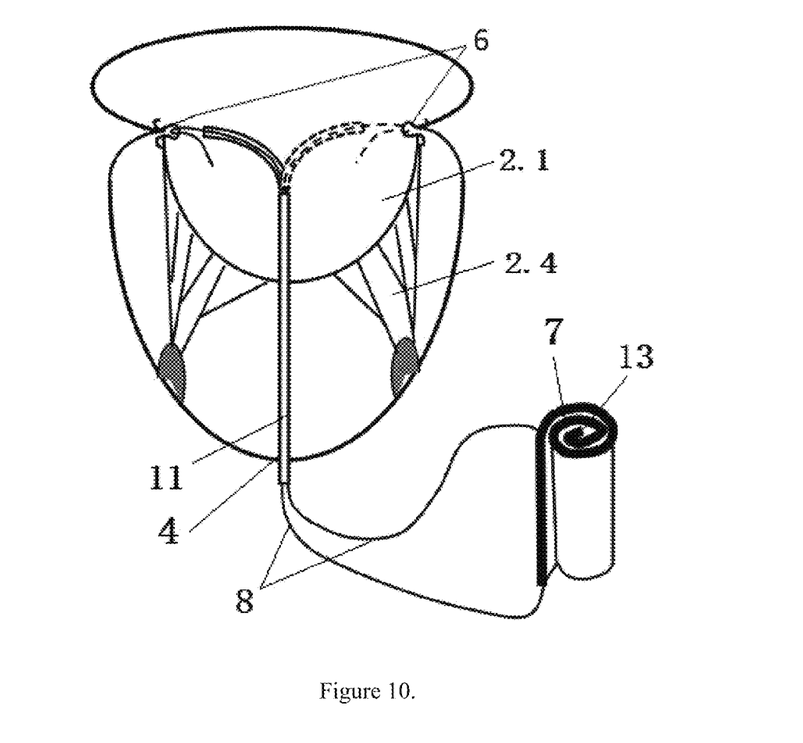
FIG. 10 is a schematic view showing the implantation state of a transapically-implanted mitral valve flexible closure plate blocking body according to the present invention.

In step 1, first, a small incision is made at the cardiac apex position on the left side of the chest to the cardiac apex 4 to perform a purse-string operation at the cardiac apex 4 position, a cardiac apex cannula is inserted into the left ventricle 3 from the purse string, the purse string is tightened, and the cardiac apex cannula is fixed. The cardiac apex cannula is clamped by hemostatic forceps to prevent the blood of the heart from flowing out of the implantation position; then the two guide wires 8 respectively thread on the connecting ring 6.2 of the hook 6, and the two hooks 6 of the connecting ring 6.2 threaded with the guide wire 8 are respectively implanted in the left and right mitral valve annuluses 2.1 of the anterior-posterior leaflet junction 5. The specific method is as follows: firstly, the first guide wire 8 threads the connecting ring 6.2 of the first hook 6, and then the first hook 6 is placed in the hook implantation catheter 9, the hemostatic forceps of the cardiac apex cannula are loosened, the hook implantation catheter 9 enters from the small incision on the left chest into the left ventricle 3 through the cardiac apex cannula and reaches the mitral valve annulus 2.1 position at two ends of the gap between the anterior leaflet 2.2 and the posterior leaflet 2.3 of the mitral valve, the first hook 6 is pushed out from the front end of the hook implantation catheter 9 by a push rod, the barb 6.1 is pushed out to deploy, and the barb 6.1 is inserted into the left end position of the mitral valve annulus 2.1 by its elasticity. The hook implantation catheter 9 is then withdrawn and the cardiac apex cannula is clamped by the hemostatic forceps. In the same way, the second guide wire 8 threads the connecting ring 6.2 of the second hook 6, then the second hook 6 is placed in the hook implantation catheter 9, the hemostatic forceps of the cardiac apex cannula are loosened, the hook implantation catheter 9 enters the left ventricle 3 through the cardiac apex cannula, and the barb 6.1 of the second hook 6 is inserted in the right end position of the mitral valve annulus 2.1. Thus, after the two hooks 6 are implanted, the hook implantation catheter 9 is withdrawn. At this time, two ends of each of the guide wires 8 passing through the hook 6 are led through a cardiac apex catheter, and the cardiac apex catheter is clamped with the hemostatic forceps to prevent bleeding of the heart.

In step 2, in vitro, the lower left portion of the flexible closure plate 7 is fixed to a left guide ring 13 and the lower right portion is fixedly coupled to a right guide ring 13. Alternatively, when it is about to manufacture a flexible closure plate 7, the guide ring 13 is formed as a single piece together with the flexible closure plate 7. One of the ends of the two guide wires 8 which are led is respectively fixedly connected to the upper portion of the flexible closure plate 7 on the same side, and the other end respectively passes through the guide rings 13 on the same side. That is, one end of the first guide wire 8 is fixedly connected to the upper left portion of the flexible closure plate 7, and the other end of the first guide wire 8 passes through the left guide ring 13 fixed on the flexible closure plate 7. One end of the second guide wire 8 is fixedly connected to the upper right portion of the flexible closure plate 7, and the other end of the second guide wire 8 passes through the right guide ring 13 fixed to the flexible closure plate 7.

The lower base of the flexible closure plate 7 is fixedly connected to one end of the pull wire 10 while the support bar 14 is fixedly embedded in the edge of the lower base of the flexible closure plate 7. Alternatively, when it is about to manufacture the flexible closure plate 7, the guide ring 13, the support rod 14, and one end of the pull wire 10 are formed together with the flexible closure plate 7 as a single piece.

The flexible closure plate 7 is tightly crimped into an elongated cylinder along their mutually parallel upper or lower bases. The flexible closure plate 7 is placed together with the guide ring 13, the support rod 14, and one end of the pull wire 10 into a closure plate implantation catheter 11. The hemostatic forceps of the cardiac apex cannula are loosened. The closure plate implantation catheter 11 is implanted from a small incision on the left side of the chest, and enters into the left ventricle 3 through a cardiac apex cannula. At this time, the guide wire 8 passing through the guide ring 13 is guided from the cardiac apex 4 in vitro through the closure plate implantation catheter 11, and the other end of the pull wire 10 also protrudes in vitro via the closure plate implantation catheter 11.

In step 3, the flexible closure plate 7 is pushed out from the closure plate implantation catheter 11 to deploy inside the left ventricle 3, the in vitro ends of the two guide wires 8 passing through the guide ring 13 are adjusted, and the guide wire 8 is tensioned so that the upper left and upper right portions of the flexible closure plate 7 are respectively located at the hook 6 position on the same side, and the flexible closure plate 7 is fixed at the anterior and posterior leaflet junction 5. The pull wire 10 is adjusted such that the lower base of the flexible closure plate 7 is tensioned by the other end of the pull wire 10.

In step 4, the closure plate implantation catheter 11 is withdrawn, the cardiac apex cannula is clamped, the purse string is loosened, the cardiac apex cannula is removed, and the purse string is tightened to prevent bleeding. The ends of the guide wire 8 and the pull wire 10 pass through the fixation plug 12, the fixation plug 12 is pushed to the cardiac apex 4 position, the purse string is loosened, the fixation plug 12 is placed on the cardiac apex 4, and the purse string is tightened and fixed. After adjusting the pulling force of the pull wire 10 and the guide wire 8 to the optimum, the pull wire 10 and the guide wire 8 are locked by the fixation plug 12, and the excessive pull wire 10 and the guide wire 8 outside the fixation plug 12 are cut off. One end of the fixation plug 12 is small and protrudes into the cardiac apex 4, and the other end has a large area and is close to the surface of the cardiac apex 4. A hole is formed in the middle of the fixation plug 12. The pull wire 10 is led out from the hole and locked by the fixation plug 12, so that the force of the pull wire 10 is uniformly distributed on the surface of the cardiac apex 4.

In step 5, the small incision on the left chest is sutured, and the implantation process of the mitral valve flexible closure plate blocking body is completed.

During diastoles, the mitral valve 2 is opened, and the blood flows from the left atrium 1 into the left ventricle 3 through the two channels between the anterior leaflet 2.2, the posterior leaflet 2.3, and the flexible closure plate 7. During systoles, the anterior leaflet 2.2 and the posterior leaflet 2.3 are closed, the edges of the leaflets squeeze the flexible closure plate 7, so that the flexible closure plate 7 is slightly deformed and the edges of the leaflets and the slightly deformed flexible closure plate 7 are tightly bound together, thereby blocking the regurgitation channel of the mitral valve 2 and effectively preventing the regurgitation of the mitral valve 2.

The invention claimed is:

1. A transapically-implantable mitral valve system, comprising: a flexible closure plate (7), a left and right guide wire (8), a left and right guide ring (13) and a fixation plug (12), wherein the fixation plug (12) is configured to be fixedly implanted at a cardiac apex (4) of the heart, the flexible closure plate (7) is intended to be used at an anterior and posterior leaflet junction of the heart, first and second hooks each being is configured to be fixedly implanted in either one of the left and right positions on a mitral valve annuluses (2.1) at the anterior and posterior leaflet commissures, the left and right guide wire (8) respectively pass through the first and second hooks (6) on the same side and are fixedly connected to the flexible closure plate (7) in the upper portion on the same side, a lower left portion and a lower right portion of the flexible closure plate (7) are fixedly connected with one guide ring (13) each, and the left and right guide wire (8) respectively pass through the guide ring (13) on the same side and are fixedly connected to the fixation plug (12), wherein each of the first and second hooks (6) is composed of two portions, a barb (6.1) and a connecting ring (6.2).

2. The transapically-implantable mitral valve system according to claim 1, characterized in that a support rod (14) is embedded in the edge of the lower base of the flexible closure plate (7) along the lengthwise direction of the lower base, the lower base of the flexible closure plate (7) is fixedly connected to one end of a pull wire (10), and the other end of the pull wire (10) is fixedly connected to the fixation plug (12).

3. The transapically-implantable mitral valve system according to claim 2, characterized in that there is a plurality of pull wires (10), the plurality of pull wires (10) has one end uniformly connected to the flexible closure plate (7) along the lengthwise direction of the lower base of the flexible closure plate (7), and the other end of the plurality of pull wires (10) is fixedly connected to the fixation plug (12).

4. The transapically-implantable mitral valve system according to claim 2, characterized in that the pull wire (10) is made from an expanded polytetrafluoroethylene material, and the support rod (14) is made from a rigid material.

5. The transapically-implantable mitral valve system according to claim 1, characterized in that the flexible closure plate (7) has a longitudinal cross section of an inverted isosceles trapezoidal structure and the flexible closure plate (7) can be curled into an elongated cylinder along the upper base or the lower base.

6. The transapically-implantable mitral valve system according to claim 1, characterized in that the each of the first and second hooks (6) is made from a nickel-titanium memory alloy material, the fixation plug (12) is made from a blood-compatible material, the flexible closure plate (7) is made from a blood-compatible flexible material, and the left and right guide wires (8) are made from an expanded polytetrafluoroethylene material.

7. A method for implanting a transapically-implanted mitral valve system according to claim 1, characterized in that a small incision is made at the cardiac apex position on the left side of the chest to the cardiac apex (4) to perform a purse-string operation at the cardiac apex (4) position, a cardiac apex cannula is inserted into the left ventricle (3) from the purse string, and the purse string is tightened to fix the cardiac apex cannula, and the method further comprises the following steps:

A. each of the left and right guide wire (8) threads a hook of the first and second hooks, the hook (6) is placed in a hook implantation catheter (9), the hook implantation catheter (9) enters the left ventricle (3) through the cardiac apex cannula and reaches the anterior and posterior leaflet junction, the hook (6) is pushed out from the hook implantation catheter (9) by a push rod, so that the hook (6) is inserted into the mitral valve annulus (2.1); first and second hooks (6) are respectively implanted in the left and right positions on a mitral valve annulus (2.1) at the anterior and posterior leaflet commissures; and the hook implantation catheter (9) is withdrawn after the first and second hooks (6) are implanted, and two ends of each of the left and right guide wire (8) passing through the hook (6) are led through a cardiac apex catheter;

B. Externally to the heart, the flexible closure plate (7) and the guide ring (13) are integrally formed into one whole piece, one end of each of the left and right guide wire (8) is fixedly connected with the upper portion of the flexible closure plate (7) on the same side, respectively, and the other end passes through the guide ring (13) on the same side; the flexible closure plate (7) is then crimped into a cylinder, the entire piece of the cylinder is placed in a closure plate implantation catheter (11), the closure plate implantation catheter (11) enters into the left ventricle (3) through the cardiac apex cannula, the flexible closure plate (7) is pushed out to deploy, the left and right guide wires (8) passing through the guide ring (13) are led in vitro through the closure plate implantation catheter (11), and finally the left and right guide wires (8) are tensioned so that the upper left and upper right portions of the flexible closure plate (7) are respectively located at the hook (6) position on the same side; and C. the closure plate implantation catheter (11) is withdrawn, the cardiac apex cannula is removed, and the left and right guide wires (8) are tightened with the fixation plug (12).

8. The method for implanting a transapically-implanted mitral valve system according to claim 7, characterized in that in step B, the lower base of the flexible closure plate (7) is fixedly connected to one end of the pull wire (10) in vitro, while the support rod (14) is fixedly embedded in the edge of the lower base of the flexible closure plate (7), and the flexible closure plate (7) together with the guide ring (13), the support rod (14) and one end of the pull wire (10) is placed in the closure plate implantation catheter (11).

9. The method for implanting a transapically-implanted mitral valve system according to claim 7, characterized in that in step A, one end of each of the left and right guide wire (8) threads the connecting ring (6.2) portion of the hook (6), and a barb (6.1) portion of the hook (6) is partially inserted into the mitral valve annulus (2.1) of the heart.

\* \* \* \* \*